United States Patent [19]
Pal et al.

[11] Patent Number: 5,618,966
[45] Date of Patent: Apr. 8, 1997

[54] METHOD FORMING PROTEASE INHIBITOR SYNTHETIC INTERMEDIATES

[75] Inventors: Biman Pal, Waltham; Siya Ram, Winchester; Bing Cai, Woburn; Yesh P. Sachdeva, Concord; Jaechul Shim, Cambridge; Salah A. Zahr, Acton; Emile Al-Farhan, W. Roxbury; Richard Gabriel, Swampscott, all of Mass.

[73] Assignee: Pharm-Eco Laboratories, Incorporated, Lexington, Mass.

[21] Appl. No.: 442,117

[22] Filed: May 16, 1995

Related U.S. Application Data

[62] Division of Ser. No. 271,619, Jul. 7, 1994, Pat. No. 5,475,138.

[51] Int. Cl.$^6$ .................. C07C 229/34; C07C 215/28; C07C 213/00; C07C 227/02; C07D 403/12
[52] U.S. Cl. .................. 560/16; 548/313.7; 558/408; 558/452; 560/34; 564/32; 564/61; 564/152; 564/159; 564/197; 564/198; 564/343; 564/355; 564/356; 564/357; 564/358; 564/342; 564/418; 564/495; 564/503
[58] Field of Search .................. 564/32, 61, 152, 564/159, 197, 198, 495, 503, 343, 344, 355, 356, 357, 358, 418, 342; 560/16, 34; 558/408, 452; 548/313.7

[56] References Cited

U.S. PATENT DOCUMENTS

| | | | |
|---|---|---|---|
| H725 | 2/1990 | Gordon | 548/533 |
| 2,139,123 | 12/1938 | Hass et al. | 564/503 |
| 2,157,386 | 5/1939 | Johnson | 564/495 |
| 2,587,572 | 2/1952 | Tryon | 564/503 X |
| 2,673,880 | 3/1954 | Eldred et al. | 564/503 X |
| 2,937,185 | 5/1960 | Biel | 564/503 X |
| 2,941,004 | 6/1960 | Pinson et al. | 564/503 X |
| 3,111,542 | 11/1963 | Doran et al. | 564/503 |

(List continued on next page.)

FOREIGN PATENT DOCUMENTS

| | | |
|---|---|---|
| 0389898A2 | 10/1990 | European Pat. Off. |
| 0449191A1 | 10/1991 | European Pat. Off. |
| 0657415A1 | 6/1995 | European Pat. Off. |
| 2200115A | 7/1988 | United Kingdom. |
| WO92/08699 | 5/1992 | WIPO. |
| WO93/23368 | 11/1993 | WIPO. |
| WO95/01323 | 1/1995 | WIPO. |

OTHER PUBLICATIONS

D. Brillon, and G. Sauvé, "Silica Gel–Catalyzed Knoevenagel Condensation of Peptidyl Cyanomethyl Ketones with Aromatic Aldehydes and Ketones. A Novel Michael Acceptor Functionality for C–Modified Peptides: The Benzylidene and Alkylidene Cyanomethyl Ketone Function", *J. Org. Chem.* 57:1838–1842 (1992).

H. Sasai, et al., "Diastereoselective Catalytic Asymmetric Nitroaldol Reaction Utilising Rare Earth Li–(R)–Binol Complex. A Highly Efficient Synthesis of Norstatine", *Tetrahedron Letters*, 35(33): 6123–6126 (1994).

D. A. Evans, et al., et al., "Synthetic Applications of Trimethylsilyl Cyanide. An Efficient Synthesis of β–Aminomethyl Alcohols," *J. Org. Chem.*, 39(7):914–917 (1974).

S. Ram and R. E. Ehrenkaufer, "A Facile Synthesis of α–Amino Esters Via Reduction of α–Nitro Esters Using Ammonium Formate as a Catalytic Hydrogen Transfer Agent," *Synthesis; Communications*, 133–135 (Feb. 1986).

T. Imai, et al., "Organoboron Compounds in Organic Synthesis. 2. Asymmetric Reduction–of–Dialkyl Ketones with (R,R)–or (S,S)–2,5–Dimethylborolane," *J. Am. Chem. Soc.*, 108:7402–7404 (1986).

E. J. Corey, et al., "A Stable and Easily Prepared Catalyst for the Enantioselective Reduction of Ketone. Applications to Multistep Syntheses," *J. Am. Chem. Soc.*, 109:77925–7926 (1987).

H. C. Brown, et al., "Chiral Synthesis via Organoboranes. 15.Selective Reductions. 42. Asymmetric Reduction of Representative Prochiral Ketones with Potassium 9–O–(1,2:5, 6–Di–O–isopropylidene–α–D–glucofuranosyl)–9– boratabicyclo[3.3.1]–nonane," *J. Org. Chem.*, 53:1231–1238 (1988).

A.G.M. Barrett, et al., "Transfer Hydrogenation: A Stereospecific Method for the Conversion of Nitro Alkanes into Amines," *Tetrahedron Letters*, 29(45):5733–5734 (1988).

A. Dondoni, et al., "Iterative, Stereoselective Homologation of Chiral Polyalkoxy Aldehydes Employing 2–(Trimethylsilyl)thiazole as a Formyl Anion Equivalent. The Thiazole Route to Higher Carbohydrates," *J. Org. Chem.*, 54:693–702 (1989).

M. M. Midland, et al., "Asymmetric Reductions of Prochiral Ketones with Lithium [2–[2–(Benzyloxy)ethyl]–6,6–dimethylbicyclo [3.1.1–3]–nonyl]–9–boratabicyclo[3.3.1] nonane (Lithium NB–Enantride) and its Derivatives," *J. Org. Chem.*, 56:1068–1074 (1991).

D. Tourwe, et al. "A New Method for the Solid Phase Synthesis of Hydroxyethylamine Peptide Bond Isosteres: Synthesis of an HIV–1 Protease Inhibitor and of a β–Casomorphin–5 Analogue," pp. 5499–5502 (1990).

D. C. Baker and S. R. Putt, "C–Acylation of Nitromethane. A Syntheic Route to α–Nitroketones," *Synthesis; Communications*, 478–479 (Jun. 1978).

*Primary Examiner*—Floyd D. Higel
*Attorney, Agent, or Firm*—Hamilton, Brook, Smith & Reynolds, P.C.

[57] ABSTRACT

The present invention relates to a method of forming a 1,3-diamino-3-substituted-2-propanol chemical intermediate from which various chemicals, such as selected protease-inhibitors and other drugs, as well as polymers, can be synthesized.

This method includes contacting a nitromethyl amino acid compound with at least one reducing agent to form the 1,3-diamino-3-substituted-2-propanol chemical intermediate.

4 Claims, No Drawings

U.S. PATENT DOCUMENTS

| | | | |
|---|---|---|---|
| 4,604,402 | 8/1986 | Godfrey et al. | 514/333 |
| 4,616,088 | 10/1986 | Ryono et al. | 546/336 |
| 4,692,455 | 9/1987 | Gordon | 514/332 |
| 4,740,508 | 4/1988 | Weller et al. | 514/255 |
| 4,749,792 | 6/1988 | Natarajan et al. | 546/312 |
| 4,898,977 | 2/1990 | Herold | 564/191 |
| 4,918,235 | 4/1990 | Scholl et al. | 564/503 |
| 5,223,535 | 6/1993 | Hanson et al. | 514/489 |
| 5,278,148 | 1/1994 | Brauca et al. | 514/19 |

METHOD FORMING PROTEASE INHIBITOR SYNTHETIC INTERMEDIATES

This application is a Divisional of U.S. Ser. No. 08/271,619 filed Jul. 7, 1994 and issued as U.S. Pat. No. 5,475,138, Dec. 12, 1995, which is incorporated herein by reference in its entirety.

BACKGROUND OF THE INVENTION

The inhibition of various proteases has application in treating many medical conditions, such as Alzheimer's disease, retroviral infections, hypotension and hypertension. Many protease-inhibitor compounds have been identified. However, the methods for synthesizing these protease-inhibitor compounds are often complex and/or expensive. Consequently, methods are needed to produce protease-inhibitor compounds through simpler and/or less expensive processes.

SUMMARY OF THE INVENTION

The present invention relates to a method of forming a 1,3-diamino-3-substituted-2-propanol chemical intermediate represented by the following structural formula (structural formula I):

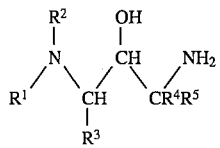

and salts thereof, wherein $R^1$ is a protecting group and $R^2$ is selected from the group consisting of —H, C1–C18 alkyl, aryl, heteroaryl, acetyl and tosyl.

Additionally, $R^3$ is the side-chain of an amino acid wherein said side-chain is located α to the amino group of the amino acid. Suitable amino acids include natural and synthetic α-amino acids, such as alanine, cysteine, 3,5-dibromotyrosine, 3,5-diiodotyrosine, glutamine, glycine, histidine, hydroxylysine, isoleucine, leucine, methionine, phenylalanine, serine, threonine, thyroxine, tryptophane, tyrosine, valine and α-aminobutyric acid. In addition, wherein the amino acid has a chiral center, the side-chain may be from either the D or L isomer of the amino acid. Further, the amino acid may optionally be substituted with one or more substitutents, such as halogen, hydroxyl, sulfonate, C1–C3 alkyl, C1–C3 alkoxy and acyl.

Furthermore, $R^4$ and $R^5$ are each independently selected from the group consisting of —H, alkyl, aryl, nitrile and alkoxycarbonyl. However, it is preferred that $R^4$ and $R^5$ are not both alkoxycarbonyl groups.

This method includes contacting a nitromethyl amino acid compound with at least one reducing agent to form said chemical intermediate. A suitable nitromethyl amino acid compound is represented by the following structural formula (structural formula II):

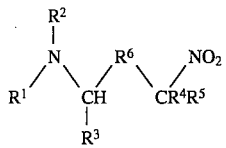

wherein $R^6$ is either

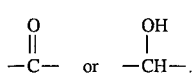

The benefits of this invention include the ability to produce protease-inhibitor compounds, and other drugs, through simpler and/or less expensive synthetic processes.

DETAILED DESCRIPTION OF THE INVENTION

A chemical intermediate, as defined herein comprises a compound from which various chemicals, such as selected protease-inhibitors and other drugs, as well as polymers, can be synthesized. In a preferred embodiment, the 1,3-diamino-3-substituted-2-propanol chemical intermediate is derived from phenylalanine and comprises a 1,3-diamino-3-benzyl-2-propanol compound.

Suitable protecting groups include protecting groups which generally prevent substitution or addition reactions from occurring with a protected amino group while producing said chemical intermediate according to the method of this invention. Examples of suitable protecting groups include benzyl, t-butyloxycarbonyl (Boc), benzyloxycarbonyl (Cbz), g-fluorenylmethoxycarbonyl (f-moc), 2,2,2-trichloroethoxycarbonyl, 2-haloethoxycarbonyl, benzoyl, phthalimidyl, diphenylphosphinyl and benzenesulfonyl. Alternatively, $R^1$ and $R^2$ can be combined to form a protecting group, such as dibenzyl.

Alkyl groups of the present invention include straight-chained, branched and cyclic alkyl radicals containing up to about 18 carbons. Suitable alkyl groups may be saturated or unsaturated. Further, an alkyl group may also be substituted one or more times on one or more carbons with substitutents selected form the group consisting of C1–C6 alkyl, C3–C6 heterocycle, aryl, halo, hydroxy, amino, alkoxy and sulfonyl. Additionally, an alkyl group may contain up to 3 heteroatoms. Suitable heteroatoms include nitrogen, oxygen and sulfur.

Aryl groups of the present invention include aryl radicals which may optionally contain up to 3 heteroatoms. An aryl group may also be optionally substituted one or more times with an aryl group or a lower alkyl group. Suitable aryl groups include, for example, phenyl, naphthyl, tolyl, imidazolyl, pyridyl, pyrroyl, thiophenyl, pyrimidyl, thiazolyl and furyl groups.

In one embodiment of the method of this invention, a 1,3-diamino-3-substituted-2-propanol chemical intermediate is formed through two successive reductions of a nitromethyl amino acid compound, having the structure of structural formula II wherein $R^6$ is a carbonyl group (hereinafter a "3-amino-3-substituted-2-oxo-1-nitropropane").

In the first reduction, a 3-amino-3-substituted-2-oxo-1-nitropropane is mixed, in solution, with a carbonyl reducing agent to form a salt of a 1-nitro-3-amino-3-substituted-2-propanol compound, wherein said 1-nitro-3-amino-3-substituted-2-propanol compound has the following structural formula (structural formula III):

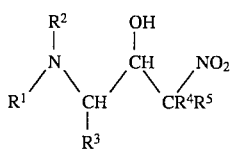

The amount of the carbonyl reducing agent used is an amount which will reduce and hydrogenate at least a portion of the 3-amino-3-substituted-2-oxo-1-nitropropane. Typically, from about 0.1 moles to about 100 moles of a carbonyl reducing agent are used per mole of 3-amino-3-substituted-2-oxo-1-nitropropane.

A carbonyl reducing agent, suitable for the method of this invention, is a chemical or combination of chemicals which will react with a 3-amino-3-substituted-2-oxo-1-nitropropane to reduce and hydrogenate the carbonyl group, but will generally not affect the nitro group. Suitable carbonyl reducing agents include, for instance, sodium borohydride, lithium borohydride, borane, disiamylborane, 9-bora-bicyclo [3.3.1]nonane, lithium Tri-Tert-Butoxyaluminumhydride, lithium triethylborohydride and lithium tri(sec-butyl) borohydride.

Suitable solvents for the solution include organic solvents, such as alcohols, esters, ethers and tetrahydrofuran.

It is understood that the 3-amino-3-substituted-2-oxo-1-nitropropane, the carbonyl reducing agent and the solvent may be combined concurrently, sequentially, or in any order or combination. It is also understood that the 3-amino-3-substituted-2-oxo-1-nitropropane may be added as a solid or in solution. It is further understood the carbonyl reducing agent may be added as a solid, liquid, in solution or any combination thereof.

Examples 3 to 6 further describe the reduction of 3-amino-3-benzyl-2-oxo-1-nitropropane compounds to 1-nitro-3-amino-3-benzyl-2-propanol compounds.

The 3-amino-3-substituted-1-nitro-2-propanol can be either in an optically pure form, such as a( 2S–3S) diastereomer or a (2S–3S)-diastereomer, or in a racemic mixture. The 2S diastereomer is preferred. By using chiral reducing agents, the first reduction of 3-amino-3-substituted-2-oxo-1-nitropropane can preferentially produce either the 2S or the 2R diastereomer of 3-amino-3-substituted-1-nitro-2-propanol. Chiral reducing agents suitable for preferentially forming the 2S diastereomer include combinations of a carbonyl reducing agent, such as lithium aluminum hydride, lithium borohydride or sodium borohydride, with a pure optically active compound, such as an amino alcohol, sugar or hydroxyalkaloid. Typically, a chiral reducing agent is about 25% to about 75% (w/w) carbonyl reducing agent and about 25% to about 75% (w/w) optically active compound. A preferred chiral reducing agent for forming the 2S-diastereomer comprises lithium aluminum hydride and (–) quinine. Other suitable chiral reducing agents include 2,5-dimethylborolane, as described in Imai e al., *J. Am. Chem. Soc.*, 108:7402 (1986), K-glucoride, as described in Brown et al., *J. Org. Chem.*,53:1231 (1988), NB-Enantride, as described in Midland et al., *J. Org. Chem.*, 56:1068 (1991), borane with a chiral oxazaborolidine catalyst, as described in Corey et al., *J. Am. Chem. Soc.*, 109:7925 (1987), R-Alpine-Hydride, obtainable from Aldrich Chemical Co., and S-Alpine-Hydride, also obtainable from Aldrich Chemical Co.

Alternatively, preferential formation of a diastereomer can occur through the use of a sterically large (or bulky) carbonyl reducing agent.

To preferentially form a diastereomer, a catalytic amount of a chiral reducing agent is mixed with a 3-amino3-substituted-1-nitro-2-propanol in an organic solvent and then refluxed at about –10° C. to about 40° C. to form the preferred diastereomer. A catalytic amount is typically defined as between about 5% and about 50% (w/w) of the 3-amino-3-substituted-1-nitro-2-propanol. Suitable organic solvents include alcohols, esters, ethers and tetrahydrofuran.

During the second reduction, the 1-nitro-3-amino-3-substituted-2-propanol compound, or salt thereof, is then mixed in solution with a nitro reducing agent and is thereby reduced to form a 1,3-diamino-3-substituted-2-propanol chemical intermediate having the structure of structural formula I. During reaction, temperature is maintained between about –40° C. and the reflux temperature of the solvent used. The preferred reaction temperature range is from about 20° C. to about 30° C.

In a preferred embodiment, the nitro reducing agent comprises a hydrogen source in the presence of a hydrogenation catalyst. Suitable hydrogen sources include, for instance, formic acid, soluble formic acid salts, such as ammonium formate, tetrahydronaphthalene and hydrogen. The amount of the hydrogen source used is an amount which will reduce and hydrogenate at least a portion of the 3-amino-3-substituted-2-oxo-1-nitropropane. Typically, the amount of the hydrogen source used is from about 0.1 molar equivalents to about 100 molar equivalents per mole of 1-nitro-3-amino-3-substituted-2-propanol compound.

Hydrogenation catalysts suitable for the second reduction include, for example, palladium on charcoal, palladium hydroxide, platinum black, platinum oxide, a combination of sodium borohydride and nickel chloride, Raney nickel, or a combination of sodium borohydride and cobalt chloride. The amount of catalyst used is typically from about 0.05 molar equivalents to about 10 molar equivalents per mole of 1-nitro-3-amino-3-substituted-2-propanol compound.

Suitable solvents for the solution during the second reduction include organic solvents, such as alcohols, alkanes, benzene, ethers, toluene, tetrahydrofuran, or any combination thereof.

To preclude poisoning of the hydrogenation catalyst by a carbonyl reducing agent containing boron or sulfur, or wherein the 1-nitro-3-amino-3-substituted-2-propanol compound is to be isolated, after the first reduction, the salt of the 1-nitro-3-amino-3-substituted-2-propanol compound is acidified with a suitable aqueous acid to form the 1-nitro-3-amino-3-substituted-2-propanol compound. Suitable acids are those acids which will acidify the salt of the 1-nitro-3-amino-3-substituted-2-propanol compound, but not cleave the protecting group. Suitable acids include, for example, $KHSO_4$, ammonium chloride and citric acid.

Example 7 further describes the reduction of a 1-nitro-3-amino-3-benzyl-2-propanol compound to a 1,3-diamino-3-benzyl-2-propanol (or 1,3-diamino-4-phenyl-2-butanol) chemical intermediate.

In another embodiment, the nitro reducing agent, suitable for the method of this invention, is a chemical or combination of chemicals which will react to reduce and hydrogenate the nitro group to form an amino group. Suitable second reducing agents include, for instance, lithium aluminum hydride. The amount of the nitro reducing agent used is an amount which will reduce and hydrogenate at least a portion of the 1-nitro-3-amino-3-substituted-2-propanol compound. Typically, from about 0.1 moles to about 100 moles of nitro reducing agent are used per mole of 1-nitro-3-amino-3-substituted-2-propanol compound.

It is understood that the 1-nitro-3-amino-3-substituted-2-propanol compound, the nitro reducing agent and the solvent may be combined concurrently, sequentially, or in any order or combination. It is also understood that the 1-nitro-3-amino-3-substituted-2-propanol compound may be added as a solid or in solution. It is further understood the nitro reducing agent may be added as a solid, liquid, gas, slurry, solution or combination thereof.

In an alternate embodiment, 1,3-diamino-3-substituted-2-propanol chemical intermediate is formed via reduction by mixing a 3-amino-3-substituted-2-oxo-1-nitropropane nitropropane with a third reducing agent, wherein said third reducing agent reduces the carbonyl group and the nitro group to form said chemical intermediate. Suitable second reducing agents include, for instance, lithium aluminum hydride.

The amount of the third reducing agent used is an amount which will reduce at least a portion of the 3-amino-3-substituted-2-oxo-1-nitropropane to form said chemical intermediate. Typically, from about 0.1 moles to about 100 moles of a third reducing agent are used per mole of 3-amino-3-substituted-2-oxo-1-nitropropane.

It is understood that the 3-amino-3-substituted-2-oxo-1-nitropropane, the third reducing agent and the solvent may be combined concurrently, sequentially, or in any order or combination. It is also understood that the 3-amino-3-substituted-2-oxo-1-nitropropane may be added as a solid or in solution. It is further understood the third reducing agent may be added as a solid, liquid, in solution or any combination thereof.

Example 8 further describes the reduction and hydrogenation of a 3-amino-3-benzyl-2-oxo-1-nitropropane compound to form a 1,3-diamino-3-benzyl-2-propanol.

A 3-amino-3-substituted-2-oxo-1-nitropropane compound of the present invention can be produced from an amino acid represented by the following structural formula (structural formula IV):

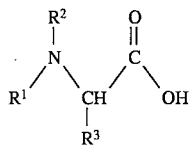

In the method for forming a 3-amino-3-substituted-2-oxo-1-nitropropane compound, said amino acid is mixed with an activating agent and an aprotic solvent under anhydrous conditions to activate said amino acid. An activating agent, as defined herein, is an agent which displaces the hydroxyl of a the carboxyl group of the amino acid with a radical suitable to make the carbonyl carbon of said carboxyl group more susceptible to nucleophilic addition. Examples of suitable activating agents include 1,1'-carbonyldiimidazole (CDI), isobutyl chloroformate, dimethylaminopropylethylcarbodiimide (EDC), dicyclohexyl carbodiimide (DCC) and N-hydroxysuccimide. For example, wherein CDI is used as activating agent, the hydroxyl group of the amino acid is replaced by an imidazolyl group.

Suitable aprotic solvents include, for instance, methylene chloride, dimethylformamide, tetrahydrofuran, dichloroethane and diethyl ether.

Anhydrous conditions, as defined herein, means no water is present in the reagents or solvent and that the reaction is performed in an inert atmosphere, such as under argon or nitrogen. Preferably, no free oxygen is present under anhydrous conditions.

It is understood that the amino acid, the activating agent and the solvent may be combined concurrently, sequentially, or in any order or combination. It is also understood that the amino acid may be added as a solid or in solution. It is further understood the activating agent may be added as a solid, liquid or in solution.

Generally, from about 0.1 moles to about 10 moles of activating agent are used per mole of amino acid. A preferred range is from about 1 mole to about 1.5 moles of activating agent per mole of amino acid.

In one embodiment, the amino acid and activating agent are refluxed to drive the reaction to completion. Typically, refluxing is performed for about 0.5 hours to about 4 hours, or until gas evolution subsides.

Further description of the formation of activated amino acid is described in Examples 1 and 2.

The activated amino acid is then combined with a nitromethane anion solution under anhydrous conditions to form a reaction mixture, and subsequently the reaction mixture is acidified to form a 3-amino-3-substituted-2-oxo-1-nitropropane compound.

The nitromethane anion solution is formed under anhydrous conditions by mixing an anhydrous base with a nitromethane compound represented by the structural formula (structural formula V)

$$CHR^4R^5NO_2$$

and optionally an aprotic solvent, such as THF. As the formation of the nitromethane anion solution is typically exothermic, and as salts of nitromethane compounds can be unstable and possibly explosive at higher temperatures, the temperature of the nitromethane anion solution is typically maintained at a cold temperature, such as about 5° C. or less.

Suitable bases are those which will deprotonate the nirtromethane compound to form a nitromethane anion. Examples of suitable anhydrous bases include metal alkoxides, such as potassium t-butoxide and sodium methoxide, sodium hydride, sodium bicarbonate and lithium diisopropylamide. The amount of the anhydrous base used is that amount which will deprotonate at least a portion of the nitromethane compound molecules to form nitromethane anions. Typically, from about 0.1 moles to about 1000 moles of anhydrous base are used per mole of nitromethane compound. It is preferred to use from about 1 mole to about 5 moles of anhydrous base per mole of nitromethane compound.

Acids suitable to acidify the reaction mixture consist of acids which will reduce pH to a sufficiently low value to prevent significant enolate formation and to react with remaining nitromethane anions, but will generally not cleave the protecting group from the 3-amino-3-substituted-2-oxo-1-nitropropane. Typically pH is reduced to about 5 or less, with a pH of 2–15 preferred. Suitable acids include, for instance, $H_2SO_4$, HCl, HBr, $H_3PO_4$, $KHSO_4$, citric acid, acetic acid and combinations thereof. Wherein the protecting group is a Boc group, acids where pH is above 3, such as $KHSO_4$, are preferred.

Further description of the formation of 3-amino-3-benzyl-2-oxo-1-nitropropane is described in Examples 1 and 2.

In a further embodiment, a second chemical intermediate is formed from the 1,3-diamino-3-substituted-2-propanol chemical intermediate, wherein the second chemical intermediate is represented by the following structural formula (structural formula VI):

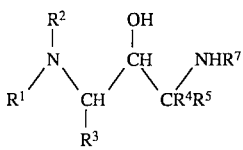

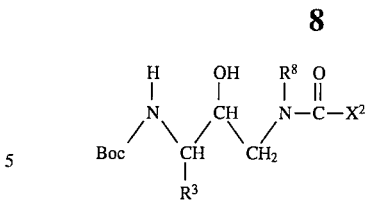

and salts thereof. $R^7$ is selected from the group consisting of alkyl, hydroxyalkyl, alkoxyalkyl, cycloalkylalkyl, heterocycloalkyl, heterocycloalkylalkyl, aryl, heteroaralkyl, and aminoalkyl radicals. Optionally, an aminoalkyl radical may be substituted up to two times with substituents selected from the group consisting of alkyl, cycloalkylalkyl, heterocycloalkyl, heterocycloalkylalkyl, aryl and heteroaralkyl radicals. Furthermore, for a di-substituted aminoalkyl radical, the substituents, combined with the nitrogen atom to which they are bound, may form a heterocycloalkyl or a heteroaryl radical.

To form the second chemical intermediate, a 1,3-diamino-3-substituted-2-propanol is mixed with an $X^1$—$R^7$ compound, where $X^1$ is a halogen radical, such as chloro or bromo, with a base. Suitable bases include bases which generally will not convert the alcohol group to an alkoxide. Preferably, the base is a mild base, such as triethylamine. See Example 9 for further description of the synthesis of 1-N-butyl-3-N-Boc-1,3-diamino-3-benzyl-2-propanol by this method.

Compounds, and pharmaceutical compositions, which can be derived from the second chemical intermediate include the compounds, and pharmaceutical compositions, described in PCT Patent Applications PCT/US91/08593, by Reed e al., and PCT/US93/04806, by Talley et al., the teachings of which are incorporated herein by reference.

In another embodiment a third chemical intermediate is formed from a 3-N-Boc-1,3-diamino-3-substituted-2-propanol, wherein the third chemical intermediate is represented by the following structural formula (structural formula VII):

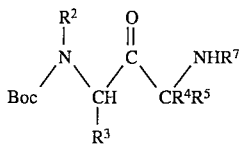

and salts thereof. A 3-N-Boc-1,3-diamino-3-substituted-2-propanol is oxidized via a Swern oxidation, by the mixing the 3-N-Boc-1,3-diamino-3-substituted-2-propanol with dimethyl sulfoxide and oxalyl chloride, and then adding a base to form said third chemical intermediate. Suitable bases include bases which generally will not convert the alcohol group to an alkoxide. Preferably, the base is a mild base, such as triethylamine. Compounds, and pharmaceutical compositions, which can be derived from the third chemical intermediate include the compounds, and pharmaceutical compositions, described in U.S. Pat. No. 4,692,455, issued to E. M. Gordon, the teachings of which are incorporated herein the reference.

In yet another embodiment, a first anti-hypotensive compound, and pharmaceutical compositions thereof, can also be formed from a 3-N-Boc-1,3-diamino-3-substituted-2-propanol compound, wherein the anti-hypotensive compound is represented by the following structural formula (structural formula VIII):

and salts thereof. $R^8$ is selected from the group consisting of hydrogen, lower alkyl, halo-substituted lower alkyl, alkaryl, heteroaryl and aminoalkyl. $X^2$ is an amino, imino acid or ester radical. Suitable amino, imino acid or ester radicals are further described in U.S. Pat. No. 4,604,402, issued to Godfrey et al., which is incorporated herein by reference.

A first anti-hypotensive compound is formed by mixing a 3-N-Boc-1,3-diamino-3-substituted-2-propanol with Cl—C(O)—$X_2$ in an anhydrous organic aprotic solvent under basic conditions, preferably with an anhydrous base. Suitable bases include bases which generally will not convert the alcohol group to an alkoxide. Preferably, the base is a mild base, such as triethylamine, other alkyl tertiary amines, aryl tertiary amines or pyridines. Anti-hypotensive, and pharmaceutical compositions, which can be produced according to this method include anti-hypotensive compounds, and pharmaceutical compositions thereof, described in U.S. Pat. No. 4,604,402.

In an additional embodiment, a second anti-hypotensive compound, or pharmaceutical compositions thereof, can also be formed from the anti-hypotensive compound of structural formula VIII, wherein the second anti-hypotensive compound is represented by the following structural formula (structural formula IX):

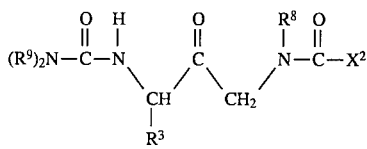

wherein $R^9$ is an alkyl or alkaryl. The compound of structural formula VIII is the oxidized through Swern oxidation, through mixing with dimethyl sulfoxide and oxalyl chloride, and then adding a weak base, such as triethylamine, to form a compound having the following structural formula (structural formula X):

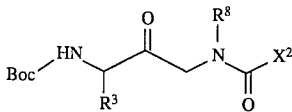

The compound of structural formula X is then contacted with an acid, such as HCl, HBr or $H_2SO_4$ to cleave the Boc protecting group and form a salt. Subsequently, the salt is mixed with a base, such as triethylamine, and with a Cl—C(O)—N($R^9$)$_2$ to form said anti-hypotensive pharmaceutical composition. Anti-hypotensive agents suitable to be formed by this method are further described in U.S. Pat. No. 4,740,508, issued to Weller et al., which is incorporated herein by reference.

Alternatively, said salt comprises a third chemical intermediate, which can be used to synthesize ureido-keto and hydroxy-substituted ureido compounds as described in U.S. Statutory Invention Registration Number H725, issued to E. M. Gordon.

The invention will now be further and specifically described by the following examples.

EXAMPLE 1

Synthesis of 3-N-Boc-amino-3-benzyl-2-oxo-1-nitropropane

In an argon atmosphere and under anhydrous conditions, 2.42 moles (391.8 g) of 1,1'-carbonyldiimidazole (CDI) and 3 liters of dry THF were mixed in a reactor. 1.89 moles (502.3 g) of Boc-phenylalanine was then added in five portions to the reactor to form a carbonyldiimidazole Boc-phenylalanine solution. Vigorous gas evolution was observed from the reaction. The mixture was refluxed for one hour and subsequently cooled to about 30° C.

In a second reactor, 2.42 moles (272 g) of potassium t-butoxide (t-Bu—O$^{31}$ K$^+$) and 15 L of THF were mixed and then cooled in an ice bath. Dropwise, 104 mL (2.46 moles; 159.6 g) of 96% nitromethane was added to the ice-cooled t-Bu—O$^-$K$^+$ solution to form a pale yellow solution.

The carbonyldiimidazole Boc-phenylalanine solution was then added dropwise to said pale yellow solution, which was concurrently cooled in an ice bath, to form a reaction mixture. After the addition, the reaction mixture was allowed to stand at room temperature for 12 hours and then was refluxed for an additional 3 hours to form 3-N-Boc-amino-3-benzyl-2-oxo-1-nitropropane in solution in THF.

After refluxing, the product solution was mixed with a 2.5 L aqueous solution (pH<1) containing 930 g H$_2$SO$_4$ and 530 g KOH to form an organic and an aqueous phase. The organic phase was then concentrated to a paste, while the aqueous phase was then extracted with ethyl acetate. The extracted ethyl acetate and the organic phase's paste were then combined and subsequently washed twice with aqueous KHSO$_4$ (final pH of the aqueous layer was 3) and then dried over anhydrous MgSO$_4$, followed by evaporation of the filtered ethyl acetate, to produce yellow, solid 3-N-Boc-amino-3-benzyl-2-oxo-1-nitropropane. The crude material was subsequently used in Examples 3, 4, 5 and 8 without purification.

An analytical specimen of 3-N-Boc-amino-3-benzyl-2-oxo-1-nitropropane was prepared by recrystallization in ethyl acetate and hexane (2:1) to give a white solid.

$^1$H NMR (300 MHz; CDCl$_3$) shifts observed were 1.40 (s,9H), 3.0–3.1 (m, 2H), 4.45 (dd, 1H), 4.9 (bd, 1H), 5.30 (dd, 2H) and 7.2–7.4 (m, 5H). The $^{13}$C NMR (75 MHz; CDCl$_3$) shifts observed were 197, 173, 155, 135, 130, 128, 83, 82, 60, 37 and 28. Elemental analysis found percents C 58.42, H 6.51 and N 9.02 with predicted percents of C 58.42, H 6.54 and N 9.09. Melting point observed was 117°–118° C.

EXAMPLE 2

Synthesis of 3-N-Cbz-amino-3-benzyl-2-oxo-1-nitropropane 111 mmoles (33.4 g) of Cbz-phenylalanine and 133 mmoles (21.6 g) of CDI were mixed with 600 mL of dry THF in a round bottom flask fitted with a reflux condenser. This mixture was then refluxed for 45 minutes to form a yellow solution.

In a second round bottom flask, 133 mmoles (14.9 g) of potassium t-butoxide, 144 mmoles (9.24 g) of 96% nitromethane and 200 mL of THF were mixed and cooled in an ice bath for 0.5 hours. The yellow solution was then added dropwise via a cannula to the ice-cooled mixture in the second round bottom flask to form a reaction mixture. After the addition, the reaction mixture was allowed to warm to room temperature and was then refluxed for 17 hours to form the 3-N-Cbz-3-amino-3-benzyl-2-oxo-1-nitropropane product in solution. After refluxing, the product solution was brick red and clear. The product solution was allowed to cool to room temperature.

After cooling, the product solution was then mixed with 250 mL of saturated aqueous KHSO$_4$ solution to acidify the mixture and then extracted five times with 100 mL aliquots of ethyl acetate. The ethyl acetate extracts were dried over anhydrous sodium sulfate. Evaporation of the filtered ethyl acetate produced a paste comprising 3-N-Cbz-3-amino-3-benzyl-2-oxo-1-nitropropane.

The 3-N-Cbz-3-amino-3-benzyl-2-oxo-1 -nitropropane residue was further purified by recrystallization from ethanol to form an ivory-colored solid.

$^1$H NMR (300 MHz; CDCl$_3$) shifts observed were 3.0–3.2 (m, 2H), 4.0–4.5 (M, 1H), 5.0–5.4 (m, 4H) and 7.2–7.5 (m, 10H). Melting point range 117° C.–121° C.

EXAMPLE 3

Synthesis of 2R,3S and 2S,3S Diastereomers of 3-N-Boc-amino-3-benzyl-1-nitro-2-propanol Using Sodium Borohydride 13.7 mmoles (0.616 g) of 3-N-Boc-amino-3-benzyl-2-oxo-1-nitropropane were dissolved in 70 mL of methanol and cooled to 0° C. Solid NaBH$_4$ (29.8 mmoles; 1.13 g) was then added to this solution to form a reaction mixture. The reaction mixture was allowed to warm to room temperature and then stirred for 14 hours. The methanol was evaporated to yield a white product residue.

The white product residue was then dissolved with 70 mL of water and 70 mL of ethyl acetate to form organic and aqueous phases. KHSO$_4$ (10 g) was also added to acidify the aqueous phase. The phases were then separated by means of a separatory funnel and the aqueous phase was subsequently extracted three times with 50 mL aliquots of ethyl acetate. The organic phases were combined, dried over anhydrous sodium sulfate, filtered and then evaporated to remove the ethyl acetate solvent and produce crude 3-N-Boc-amino-3-benzyl-1-nitro-2-propanol.

The crude product was then purified by flash chromatography on a silica gel column using 5:1 hexane/ethyl acetate. The fractions containing the desired diastereomers were separately pooled and the solvent was evaporated from each to leave a white residues.

The fraction (R$_f$=0.20) corresponding to the (22, 33) diastereomer was the minor fraction, with a yield of about 13%.

$^1$H NMR (300 MHz, CDCl$_3$) shifts observed were 1.6 (s, 9H), 2.9–3.0 (m, 2H), 3.3–3.4 (m, 2H), 3.8–9 (m, 1H), 4.3–4.4 (m, 1H), 4.5–4.6 (m, 2H), 4.9–5.0 (m, 1H) and 7.2–7.4 (m, 5H).

The fraction (R$_f$=0.16) corresponding to the (22, 35) diastereomer was the primary fraction, with a yield of about 37%. $^1$H NMR (300 MHz, CDCl$_3$) shifts observed were 1.3 (s, 9H), 2.8 (dd, 1H), 3.15 (dd, 1H), 3.85 (m, 1H), 4.4 (m, 1H), 4.5 (t, 1H), 4.8 (d, 1H), 5.0 (d, 1H), 6.05 (bd, 1H) and 7.2–7.3 (m, 5H). The $^{13}$C (75 MHz, Acetone-d$_6$) shifts observed were 156, 140, 132, 130, 127, 82, 80, 73, 57, 37 and 28. Elemental analysis found percentages were C 57.91, H 7.18 and N 9.02 with predicted percentages of C 58.04, H 7.15 and 9.03. Melting point observed was 144°–144.5° C.

EXAMPLE 4

Synthesis of
3-N-Boc-amino-3-benzyl-1-nitro-2-propanol

Using Lithium tri(sec-butyl)Borohydride 4.05 mmoles (1.25 g) of 3-N-Boc-amino-3-benzyl-2-oxo1-nitropropane were dissolved in 100 mL of dry THF and cooled to 0° C. in an ice bath, under argon and with continuous stirring. Six mLs of 1M lithium tri-(secbutyl) butylborohydride solution in dry THF were then added dropwise to form a reaction mixture. The reaction mixture was then maintained at 0° C. for 2 hours. During the 2 hour reaction period, a minor amount of gas evolved from the reaction mixture and a light yellow color appeared. After 2 hours, the reaction was quenched by adding about 1 mL of acetone while still at 0° C.

The product residue was then mixed with 50 mL of ethyl acetate and 50 mL of 10% aqueous $KHSO_4$ solution to form organic and aqueous phases and to acidify these phases. The phases were then transferred into a separatory funnel with an additional 25 mL of ethyl acetate for rinsing and then separated. The aqueous phase was subsequently re-extracted once with a 75 mL aliquot of ethyl acetate. The organic phases were combined, washed once with brine, dried over anhydrous sodium sulfate and then evaporated by means of a rotary evaporator to from a yellow oil.

The ratio of (22,3S) and (2S,3S)diastereomers was found to be 1:1 by NMR analysis.

EXAMPLE 5

Synthesis of
3-N-Boc-amino-3-benzyl-1-nitro-2-propanol Using lithium tri-tert-butoxyaluminohydride 5.51 mmoles (1.70 g) of 3-N-Boc-amino-3-benzyl-2-oxo1-nitropropane were dissolved in 100 mL of dry THF and cooled to 0° C. in an ice bath, under argon and with continuous stirring. Nine mLs of 1M lithium tri-tert-butoxyaluminohydride solution in dry THF were then added to form a reaction mixture. A pale yellow color appeared. The reaction mixture was then maintained at 0° C. for 2.15 hours.

The reaction was then quenched by adding 50 mL of 10% aqueous $KHSO_4$ solution while still at 0° C. Upon addition, a minor amount of gas evolved from the reaction mixture and aluminum salts precipitated from solution.

The product residue was then transferred to a separatory funnel with 100 mL of ethyl acetate to form organic and aqueous phases. The phases were separated and then the aqueous phase was subsequently extracted once with a 50 mL aliquot of ethyl acetate. The organic phases were combined, washed once with brine, dried over anhydrous sodium sulfate and then evaporated by means of a rotary evaporator to from a white solid.

The ratio of (22,3S) and (2S,3S)diastereomers was found to be 1:3 by NMR analysis.

EXAMPLE 6

Synthesis of
3-N-Cbz-amino-3-benzyl-1-nitro-2-propanol

To one gram of 3-N-Cbz-amino-3-benzyl-2-oxo-1-nitropropane, dissolved in 30 mL of methanol, was added 0.21 g of $NaBH_4$ to form a reaction mixture. The reaction mixture was allowed to stand at room temperature and then stirred for 4 hours. The methanol was evaporated under reduced pressure to yield a product residue.

The product residue was then mixed with 5 mL of aqueous saturated ammonium chloride solution and extracted twice with 30 mL of aliquots of ethyl acetate to form organic and aqueous phases. The phases were then separated by means of a separatory funnel. The organic phase was dried over anhydrous magnesium sulfate, filtered and then evaporated to remove the ethyl acetate solvent and produce a fluffy white solid.

The ratio of (22,3S) and (2S,3S) diastereomers was found to be 18:70 by NMR analysis.

EXAMPLE 7

Synthesis of
3-N-Boc-1,3-diamino-3-benzyl-2-propanol Using Ammonium Formate To 14.5 g of 3-N-Boc-amino-3-benzyl-1-nitro-2-propanol, dissolved in 150 mL of anhydrous methanol and under argon, was added 1.1 g of Pd/C (5%) catalyst. Ammonium formate (28.1 g) was then added in one portion. An additional 250 mL of methanol was subsequently added to facilitate stirring. The mixture was then stirred overnight.

The reaction mixture was then filtered to remove precipitates of ammonium formate. The filtrate was then concentrated to give a white solid.

$^1$H NMR (300 MHz, Acetone $D_6$) shifts observed were 1.40 (s, 9H), 2.80 (dd, 1H), 2.95–3.05 (m, 3H), 3.15–3.25 (m, 2H), 3.70 (m, 1H), 3.80 (m, 1H), 7.20–7.30 (m, 5H) and 8.20 (s, 2H). Melting point observed was 134°–136° C.

EXAMPLE 8

Synthesis of
3-N-Boc-1,3-diamino-3-benzyl-2-propanol Using Lithium Aluminum Hydride 2.92 mmoles (1 g) of 3-N-Boc-amino-3-benzyl-2-oxo-1-nitropropane were dissolved in dry THF and cooled to 0° C. in an ice bath, under argon and with continuous stirring. 11.7 mmoles (0.44 g) of lithium aluminum hydride, dissolved in THF, was added. After gas evolution subsided, the mixture was refluxed for 3 hours and then maintained at room temperature to yield a cloudy solution. Concentrated HCl (4 mL) was then added to make the solution clear. The solution was then extracted with 200 mL of methylene chloride. The combined organic layers were washed with 150 mL of saturated sodium bicarbonate and then dried over magnesium sulfate to yield the product.

EXAMPLE 9

Synthesis of
1-N-butyl-3-N-Boc-1,3-diamino-3-benzyl-2-propanol 1.12 g of 3-N-Boc-1,3-diamino-3-benzyl-2-propanol, were dissolved in 7 mL of dimethylformamide. To this solution was added 0.54 g (3.9 mmole) 1-bromobutane dropwise. The resulting solution was maintained at 80° C. for 5 hours and then cooled to room temperature before dilution with 50 mL of ethyl ether. The resulting solution was washed with two 20 mL aliquots of water. The organic phase was dried ($MgSO_4$) and concentrated to afford a solid. Column chromatography of the crude product produced 1-N-butyl-3-N-Boc-1,3-diamino-3-benzyl-2-propanol.

Chemical Analysis

Melting points were determined with a Thomas Hoover capillary melting point apparatus and are uncorrected. Elemental analyses were performed by Atlantic Microlab, Inc., Norcross, Ga. $^1$H NMR spectra were measured at 300 MHz on a Bruker AC300 and $^{13}$C NMR spectra were measured at 75 MHz obtained on a Bruker AC300.

Equivalents

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method for producing a protease inhibitor synthetic intermediate from an N-(tert-butoxycarbonyl)-3-amino-3-substituted-2-oxo-1-nitropropane;

wherein:
    said protease inhibitor synthetic intermediate is represented by the following structural formula:

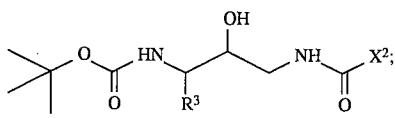

or salts thereof, wherein:

$R^3$ is a side-chain of an amino acid wherein said side-chain is located α to the amino group of the amino acid, and wherein said amino acid is selected from the group consisting of alanine, cysteine, 3,5-dibromotyrosine, 3,5-diiodotyrosine, glutamine, glycine, histidine, hydroxylysine, isoleucine, leucine, methionine, phenylalanine, serine, threonine, thyroxine, tryptophane, tyrosine, valine and α-aminobutyric acid; and $X^2$ is an amino, imino or ester radical;

said N-(tert-butoxycarbonyl)-3-amino-3-substituted-2-oxo-1-nitropropane is represented by the following structural formula:

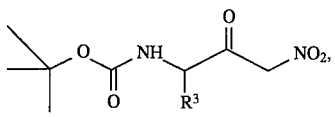

and
said method comprises the steps of:
a) reacting said N-(tert-butoxycarbonyl)-3-amino-3-substituted-2-oxo-1-nitropropane with a carbonyl group reducing agent, thereby forming an N-(tert-butoxycarbonyl)-1-nitro-3-amino-3-substituted-2-propanol compound represented by the following structural formula:

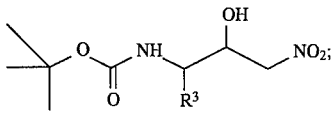

reacting said N-(tert-butoxycarbonyl)-1-nitro-3-amino-3-substituted-2-propanol with a nitro reducing agent, thereby forming a first chemical intermediate represented by the following structural formula:

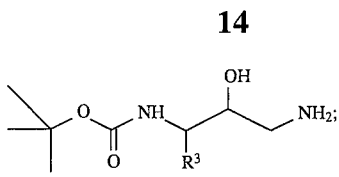

c) reacting said first chemical intermediate with Cl—C(O)—$X^2$ and with a base, thereby forming said protease inhibitor synthetic intermediate.

2. A method for producing a composition of matter from a N-(tert-butoxycarbonyl)-3-amino-3-substituted-2-oxo-1-nitropropane;

wherein:
    said composition of matter is represented by the following structural formula:

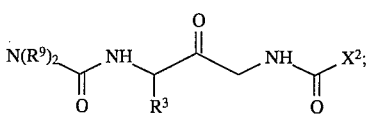

wherein:

$R^3$ is a side-chain of an amino acid wherein said side-chain is located α to the amino group of the amino acid and wherein said amino acid is selected from the group consisting of alanine, cysteine, 3,5-dibromotyrosine, 3,5-diiodotyrosine, glutamine, glycine, histidine, hydroxylysine, isoleucine, leucine, methionine, phenylalanine, serine threonine, thyroxine, tryptophane, tyrosine, valine and α-aminobutyric acid;

$R^9$ is an alkyl or alkaryl; and $X^2$ is an amino, imino acid or ester radical;

said N-(tert-butoxycarbonyl)-3-amino-3-substituted-2-oxo-1-nitropropane is represented by the following structural formula:

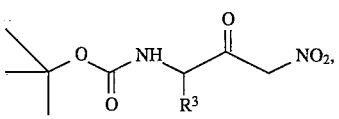

and
said method comprises the steps of:
a) reacting said N-(tert-butoxycarbonyl)-3-amino-3-substituted-2-oxo-1-nitropropane with a carbonyl reducing agent, thereby forming an N-(tert-butoxycarbonyl)-1-nitro-3-amino-3-substituted-2-propanol represented by the following structural formula:

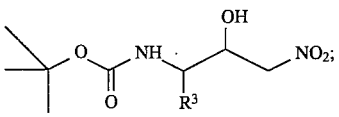

b) reacting said N-(tert-butoxycarbonyl)-1-nitro-3-amino-3-substituted-2-propanol with a nitro reducing agent, thereby forming a first chemical intermediate represented by the following structural formula:

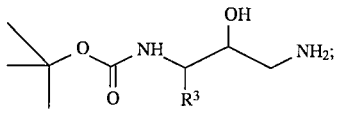

c) reacting said first chemical intermediate with Cl—C(O)—X² and with a base to form a second chemical intermediate represented by the following structural formula:

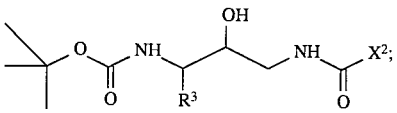

d) reacting said second chemical intermediate with dimethyl sulfoxide and oxalyl chloride to form a reaction mixture; e) reacting said reaction mixture with a base to form a third chemical intermediate represented by the following structural formula:

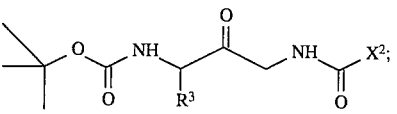

f) reacting the third chemical intermediate with an acid to cleave the tert-butoxycarbonyl group from the third chemical intermediate, thereby forming a deprotected third chemical intermediate represented by the following structural formula:

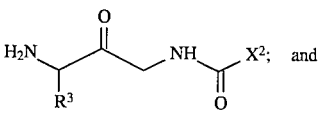

g) reacting the deprotected third chemical intermediate with a base and Cl—C(O)—N(R⁹)₂ to form said composition.

3. A method for producing a protease inhibitor synthetic intermediate from an N-(tert-butoxycarbonyl)-3-amino-3-substituted-2-oxo-1-nitropropane;
wherein:
said protease synthetic intermediate is represented by the following structural formula:

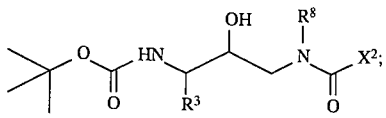

wherein:
R³ is a side-chain of an amino acid wherein said side-chain is located to the amino group of the amino acid, and wherein said amino acid is selected from the group consisting of alanine, cysteine, 3,5-dibromotyrosine, 3,5-diiodotyrosine, glutamine, glycine, histidine, hydroxylysine, isoleucine, leucine, methionine, phenylalanine, serine, threonine, thyroxine, tryptophane, tyrosine, valine and α-aminobutyric acid;
R⁸ is selected from the group consisting of alkyl, hydroxyalkyl, alkoxyalkyl, cycloalkylalkyl, heterocycloalkyl, heterocycloalkylalkyl, aryl, heteroaralkyl and aminoalkyl; and X² is an amino, imino acid or ester radical;
said N-(tert-butoxycarbonyl)-3-amino-3-oxo-1-nitropropane is represented by the following structural formula:

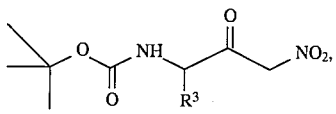

said method comprises the steps of:
a) reacting said N-(tert-butoxycarbonyl)-3-amino-3-substituted-2-oxo-1-nitropropane with a carbonyl group reducing agent, thereby forming an N-(tert-butoxycarbonyl)-1-nitro-3-amino-3-substituted-2-propanol compound represented by the following structural formula:

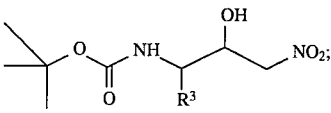

b) reacting said N-(tert-butoxycarbonyl)-1-nitro-3-amino-3-substituted-2-propanol with a nitro reducing agent, thereby forming a first chemical intermediate represented by the following structural formula:

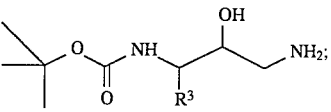

c) reacting said first chemical intermediate with X¹—R⁸ and a base, wherein X¹ is a halogen, thereby forming a compound represented by the following structural formula:

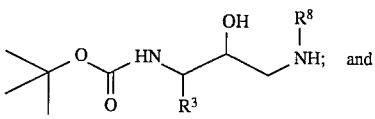

d) reacting the compound produced in c) with Cl—C(O)—X² and with a base, thereby forming said protease inhibitor synthetic intermediate.

4. A method for producing a composition of matter from a N-(tert-butoxycarbonyl)-3-amino-3-substituted-2-oxo-1-nitropropane;
wherein:
said composition of matter is represented by the following structural formula:

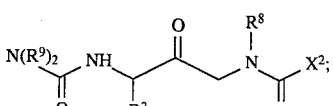

wherein:
R³ is a side-chain of an amino acid wherein said side-chain is located α to the amino group of the amino acid and wherein said amino acid is selected from the group consisting of alanine, cysteine, 3,5-dibromotyrosine, 3,5-diiodotyrosine, glutamine, glycine, histidine, hydroxylysine, isoleucine, leucine, methionine, phenylalanine, serine threonine, thyroxine, tryptophane, tyrosine, valine and α-aminobutyric acid;

$R^8$ is selected from the group consisting of alkyl, hydroxyalkyl, alkoxyalkyl, cycloalkylalkyl, heterocycloalkyl, heterocycloalkylalkyl, aryl, heteroaralkyl and aminoalkyl; and $R^9$ is an alkyl or alkaryl; and $X^2$ is an amino, imino acid or ester radical;

said N-(tert-butoxycarbonyl)-3-amino-3-substituted-2-oxo-1-nitropropane is represented by the following structural formula:

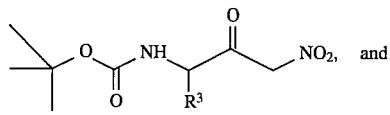, and said method comprises the steps of:

a) reacting said N-(tert-butoxycarbonyl)-3-amino-3-substituted-2-oxo-1-nitropropane with an carbonyl reducing agent, thereby forming a N-(tert-butoxycarbonyl)-1-nitro-3-amino-3-substituted-2-propanol compound represented by the following structural formula:

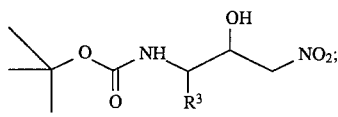

b) reacting said N-(tert-butoxycarbonyl)-1-nitro-3-amino-3-substituted-2-propanol with a nitro reducing agent, thereby forming a first chemical intermediate represented by the following structural formula:

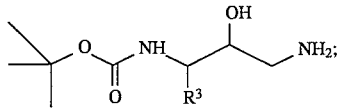

c) reacting said first chemical intermediate with $X^1$—$R^8$ and a base, wherein X is a halogen, thereby forming a compound represented by the following structural formula:

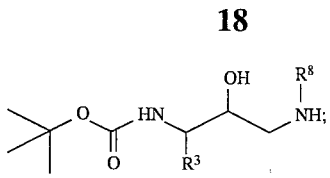

d) reacting the compound produced in C) with Cl—C(O)—$X^2$ and with a base to form a second chemical intermediate represented by the following structural formula:

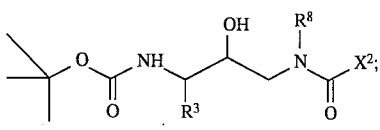

e) mixing said second chemical intermediate with dimethyl sulfoxide and oxalyl chloride to form a reaction mixture;

f) reacting said reaction mixture with a base to form a third chemical intermediate represented by the following structural formula:

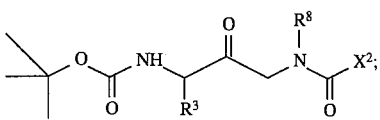

g) reacting the third chemical intermediate with an acid to cleave the tert-butoxycarbonyl group from the third chemical intermediate, thereby forming a deprotected third chemical intermediate represented by the following structural formula:

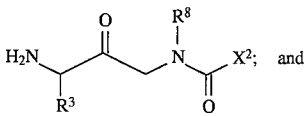 and h) reacting the deprotected third chemical intermediate with a base and Cl—C(O)—N($R^9$)$_2$ to form said composition.

* * * * *

UNITED STATES PATENT AND TRADEMARK OFFICE
CERTIFICATE OF CORRECTION

PATENT NO. : 5,618,966
DATED : April 8, 1997
INVENTOR(S) : Biman Pal, Siya Ram, Yesh P. Sachdeva, Jaechul Shim, Salah A. Zahr, Emile Al-Farhan and Richard Gabriel It is certified that error appears in the above-indentified patent and that said Letters Patent is hereby corrected as shown below:

In Column 17, line 44: After the word "wherein", delete "Xis" and insert therefor -- $X^1$ is; and--

In Column 18, line 7: After the words "produced in", delete "C)" and insert therefor --c)--.

Signed and Sealed this

Twenty-ninth Day of July, 1997

*Attest:*

BRUCE LEHMAN

*Attesting Officer*     *Commissioner of Patents and Trademarks*